US012575897B2

(12) United States Patent
Demanget et al.

(10) Patent No.: US 12,575,897 B2
(45) Date of Patent: Mar. 17, 2026

(54) NAVIGATED HANDPIECE MOTOR CURRENT SIGNAL AND POSE ESTIMATION BASED GEOFENCING

(71) Applicant: DEPUY IRELAND UNLIMITED COMPANY, Ringaskiddy (IE)

(72) Inventors: Nicolas Demanget, Boston, MA (US); Daniel Girardeau-Montaut, Grenoble (FR)

(73) Assignee: DEPUY IRELAND UNLIMITED COMPANY, County Cork (IE)

( * ) Notice: Subject to any disclaimer, the term of this patent is extended or adjusted under 35 U.S.C. 154(b) by 0 days.

(21) Appl. No.: 18/536,824

(22) Filed: Dec. 12, 2023

(65) Prior Publication Data

US 2025/0186127 A1     Jun. 12, 2025

(51) Int. Cl.
*A61B 5/00*      (2006.01)
*A61B 17/14*     (2006.01)
*A61B 34/20*     (2016.01)

(52) U.S. Cl.
CPC .............. *A61B 34/20* (2016.02); *A61B 17/14* (2013.01); *A61B 2034/2051* (2016.02)

(58) Field of Classification Search
CPC .. A61B 34/20; A61B 2034/104; A61B 17/154
See application file for complete search history.

(56) References Cited

U.S. PATENT DOCUMENTS

| | | | |
|---|---|---|---|
| 6,757,582 B2 | 6/2004 | Brisson | |
| 7,346,417 B2 | 3/2008 | Luth | |
| 2014/0222003 A1* | 8/2014 | Herndon | A61B 17/1622 606/80 |
| 2018/0325528 A1* | 11/2018 | Windolf | A61B 17/1622 |
| 2020/0268461 A1 | 8/2020 | Forstein | |
| 2020/0289133 A1 | 9/2020 | Elbanna | |
| 2022/0338938 A1 | 10/2022 | Walen | |
| 2023/0255701 A1 | 8/2023 | Post | |

OTHER PUBLICATIONS

International Search Report and Written Opinion for corresponding PCT Application No. PCT/EP2024/085403 mailed on Feb. 20, 2025.

* cited by examiner

*Primary Examiner* — Rajeev P Siripurapu
(74) *Attorney, Agent, or Firm* — Kramer & Amado P.C.

(57) ABSTRACT

A geofencing system for a surgical handpiece with a cutting surface, including: a motion tracking system configured to track a location of the surgical handpiece; and an event detector configured to: receive a current measurement signal indicating a current usage of the surgical handpiece; receive motion information regarding the surgical handpiece from the motion tracking system; determine if the cutting surface has exited a second surface of a bone opposite a first surface where the cutting surface entered the bone based upon the current measurement signal and the motion information; and stop the surgical handpiece when it is determined that the cutting surface has exited the second surface of the bone.

16 Claims, 4 Drawing Sheets

NAVIGATED HANDPIECE MOTOR CURRENT SIGNAL AND POSE ESTIMATION BASED GEOFENCING

FIELD OF THE DISCLOSURE

Various exemplary embodiments disclosed herein relate to navigated handpiece motor current signal and pose estimation based geofencing.

BACKGROUND

Robot assisted surgical systems are being used in a variety of surgical procedures. Robot assisted surgical systems include a tracking system that tracks the location of the various handpieces (e.g., saws, drills, grinders, etc.). The tracking system also tracks the location of the patient and various specific patient anatomy. The tracking system can then determine the position of the handpiece and specifically sawblades and drill bits relative to the patient anatomy. The tracking system allows for carrying out various surgical steps including sawing and drilling with precision and accuracy. The tracking system may be used with surgeries where the surgeon handles the handpiece. The tracking system assists the surgeon carrying out surgical steps precisely and accurately.

SUMMARY

A summary of various exemplary embodiments is presented below.

Various embodiments relate to a geofencing system for a surgical handpiece with a cutting surface, including: a motion tracking system configured to track a location of the surgical handpiece; and an event detector configured to: receive a current measurement signal indicating a current usage of the surgical handpiece; receive motion information regarding the surgical handpiece and the patients anatomy (such as a bone) from the motion tracking system; determine if the cutting surface has exited a second surface of a bone opposite a first surface where the cutting surface entered the bone based upon the current measurement signal and the motion information; and stop the surgical handpiece when it is determined that the cutting surface has exited the second surface of the bone.

Various embodiments are described, wherein the motion information includes a speed and direction of motion of the cutting surface.

Various embodiments are described, wherein determining if the cutting surface has exited the second surface of the bone includes determining that the current usage of the surgical handpiece has dropped and that the direction of motion is towards the second surface.

Various embodiments are described, wherein determining that the current usage of the surgical handpiece has dropped includes determining that a value of the current usage has dropped below a threshold value.

Various embodiments are described, wherein determining if the cutting surface has exited the second surface of the bone includes identifying a pattern in the current usage of the surgical handpiece indicative of the cutting surface exiting the second surface and that the direction of motion is towards the second surface.

Various embodiments are described, wherein the event detector is further configured to determine that a value of current usage has increased and that the direction of motion is towards the second surface to indicate that the surgical handpiece has entered the bone.

Further various embodiments relate to a method of geofencing a surgical handpiece with a cutting surface, including: receiving a current measurement signal indicating a current usage of the surgical handpiece; receiving motion information regarding the surgical handpiece from a motion tracking system; determining if the cutting surface has exited a second surface of a bone opposite a first surface where the cutting surface entered the bone based upon the current measurement signal and the motion information; and stopping the surgical handpiece when it is determined that the cutting surface has exited the second surface of the bone.

Various embodiments are described, wherein the motion information includes a speed and direction of motion of the cutting surface.

Various embodiments are described, wherein determining if the cutting surface has exited the second surface of the bone includes determining that the current usage of the surgical handpiece has dropped and that the direction of motion is towards the second surface.

Various embodiments are described, wherein determining that the current usage of the surgical handpiece has dropped includes determining that a value of the current usage has dropped below a threshold value.

Various embodiments are described, wherein determining if the cutting surface has exited the second surface of the bone includes identifying a pattern in the current usage of the surgical handpiece indicative of the cutting surface exiting the second surface and that the direction of motion is towards the second surface.

Various embodiments are described, further including determining that a value of current usage has increased and that the direction of motion is towards the second surface to indicate that the surgical handpiece has entered the bone.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, both their organization and method of operation, together with associated advantages will be better understood from the following description when considered in connection with the accompanying figures. Each of the figures is provided for the purposes of illustration and description, and not as a definition of the limits of the claims.

BRIEF DESCRIPTION OF DRAWINGS

So that the above-recited features of the present disclosure can be understood in detail, a more particular description, briefly summarized above, is provided by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects. The same reference numbers in different drawings may identify the same or similar elements.

DETAILED DESCRIPTION

Figure 1A:
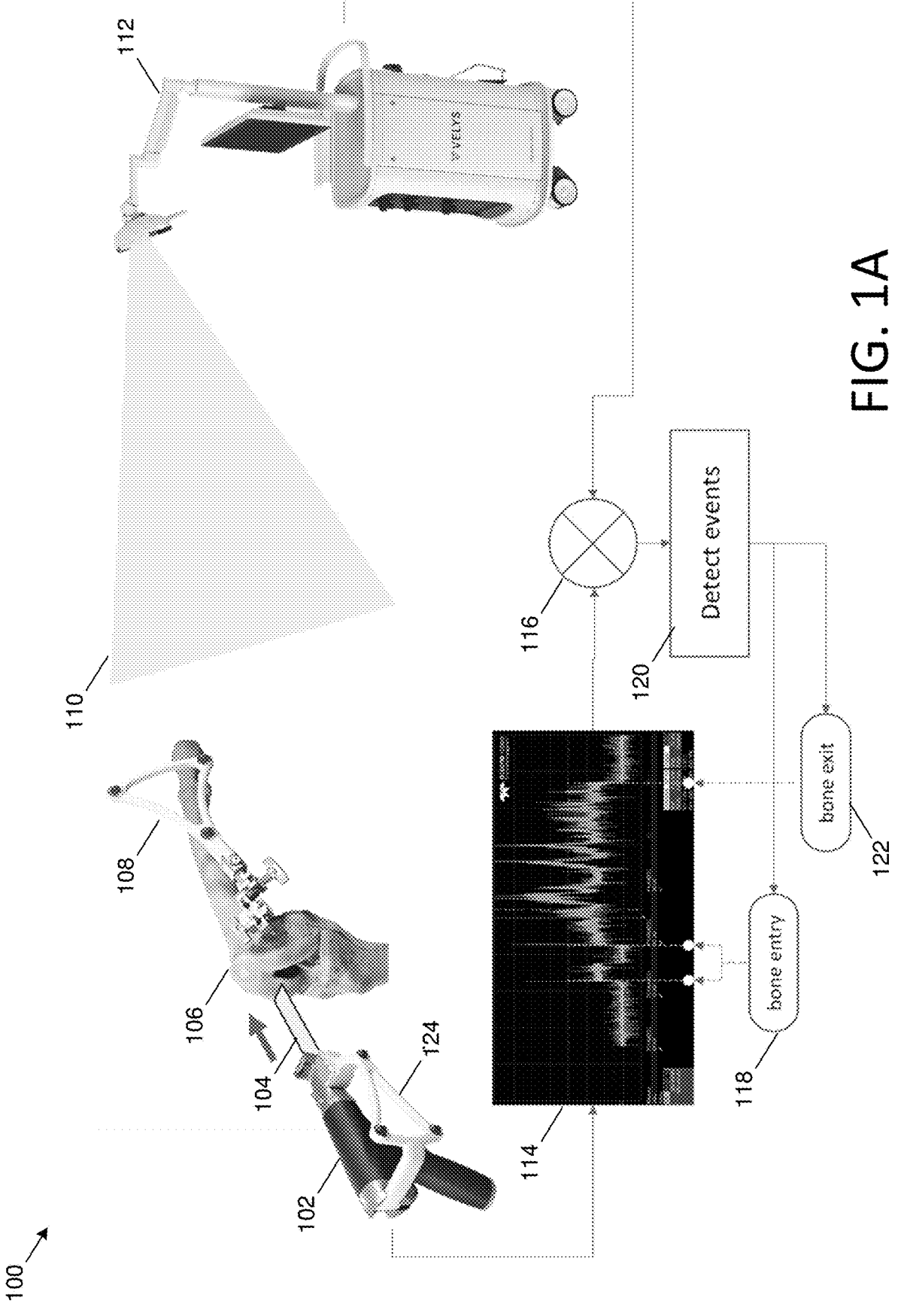
FIG. 1A illustrates an embodiment of a geofencing system for a navigation based system.

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

Several aspects of geofencing the location of tools in robotic surgical systems will now be presented with reference to various apparatuses and techniques. These apparatuses and techniques will be described in the following detailed description and illustrated in the accompanying drawings by various blocks, modules, components, circuits, steps, processes, algorithms, and/or the like (collectively referred to as "elements"). These elements may be implemented using hardware, software, or combinations thereof. Whether such elements are implemented as hardware or software depends upon the particular application and design constraints imposed on the overall system.

While robot surgical systems, robot assisted surgeries, and navigation surgeries allow for great precision and accuracy, there are situations where cuts are made or holes are drilled that there is adjacent soft tissue near the location of the cut or hole that should not be damaged during bone preparation. Even with a tracking system, it may be difficult to know exactly when a cutting blade leaves bone and engages soft tissue. This is specially the case for image-free systems where no preoperative imaging is used to generate a three dimensional model of the patients anatomy. In response, a geofencing system is described herein that determines when a cutting blade enters or leaves bone to prevent the blade from engaging with soft tissue. Throughout the description below a saw blade will be used in the description, but the geofencing system may be applied to other types of handpieces that cut, drill, grind, etc.

The embodiments of a geofencing system described herein include combining the motor current signal of the saw handpiece and the pose estimation of a navigated saw handpiece using the tracking system to enable geofencing during bone resection. The navigated handpiece could either be used with standard surgical navigation, robotics, or augmented reality (AR) headset-based navigation.

When the handpiece is turned off, no current is needed. When the handpiece is turned on, but in the air, the current reaches a first threshold. When the handpiece is turned on and entering or into the bone, a higher current is needed to cut the bone. If this current signal is used with the pose estimation of the saw handpiece relative to the bone itself, the system should be able to know whether the saw blade is fully into the bone, partially into the bone, or completely outside the bone. It is further noted that a control actuator (e.g., a trigger) may be used to control the speed of the handpiece, which causes the handpiece to use different amounts of current. In such a situation, the threshold value may account for the position of such a control actuator.

Using this information should allow the system to turn the handpiece on and off to enable geofencing during some cuts. Potential applications could be to protect the posterior soft tissues behind the tibia during the tibial cut for total knee arthroplasty (TKA), to protect the glenoid and surrounding soft tissues during the humeral cut for total shoulder arthroplasty (TSA), etc.

Geofencing may be used to prevent the surgeon from damaging soft tissues during bone preparation in an orthopedic surgery. Surgeons usually use retractors. However, some critical parts of the soft tissues may still not be properly protected, or retractors may conflict with bone arrays or instruments during a navigation or robotic surgery, resulting in an increasing risk of inaccuracy and creating some usability issues. Several fully hardware-based solutions have been explored to address this issue (tissue-sparing saw handpiece, also known as a Tuke saw for example) but have never been successful for different reasons (slower and less efficient than standard handpiece, etc.). Some other software-based solutions have been implemented successfully, but they only work with image-based solutions.

FIG. 1A illustrates an embodiment of a geofencing system for a navigation based system. The surgical system 100 includes a surgical saw 102 with a saw blade 104. A tracking array 124 is attached to the surgical saw 102. A bone 106 may have a tracking array 108 attached to it. The surgical saw 102 is to be used to cut the bone 106. A tracking system 112 is used to track the location of the surgical saw 102 and bone 106 relative to one another using the tracking array 124 and tracking array 108. Specially the cutting surface of the saw blade 104 is of most interest here, and it may be tracked based upon the tracking array 124. The tracking system may emit a light source, for example IR radiation 110 (but other types of radiation may be used or even ambient light). The IR radiation 110 reflects off of reflective spheres on the tracking array 108 and tracking array 124. The tracking system 112 includes cameras that receive images of the surgical area including the tracking arrays. The received images may be analyzed by the tracking system 112 to identify the locations of the reflective spheres. Because multiple cameras are used, the locations of the reflective spheres can be determined in three dimensions, and hence the location of the surgical saw 102 and its saw blade 104 and the bone 106. Further, the tracking system 112 can detect motion of the tracking arrays and hence the surgical saw 102 and the bone 106. It is noted that the tracking array 124 and tracking array 108 may instead use emitting elements instead of the reflective spheres. The tracking system 112 may include other known methods for tracking the location of the surgical saw 102 relative to the bone 106.

Figure 1B:
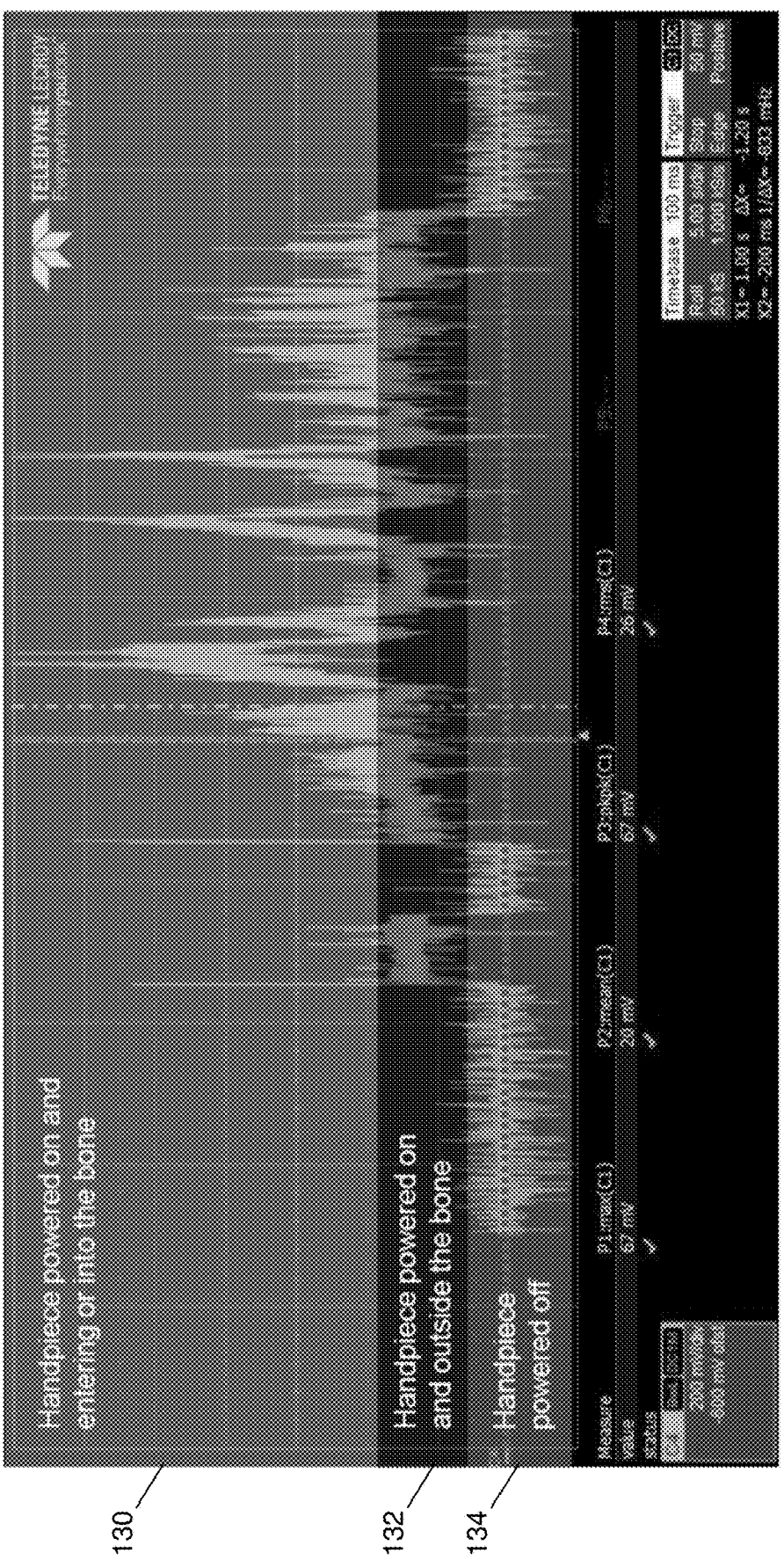
FIG. 1B illustrates the saw motor current plot in greater detail.

The geofencing system measures the current use of the surgical saw 102. An example saw motor current plot 114 is illustrated in FIG. 1A. FIG. 1B illustrates the saw motor current plot in greater detail. The plot of the current varies depending on whether the saw blade 104 is inside or entering the bone 106, is outside the bone 106, or the surgical saw 102 is off. As can be seen in the saw motor current plot 114 there are distinct current levels that the surgical saw 102 uses. When the surgical saw 102 is off, the current may be in the powered off region 134 as shown in FIG. 1B. A threshold value may be set to define this region based upon measurements and testing of the different handpieces that might be used in surgery. This may be done by the user running the saw in the air to determine the current in that situation. When the surgical saw 102 is on and the saw blade 104 is outside the bone, the current falls within the outside the bone region 132 of the plot. This region may be defined based upon measurements and testing of the different hand-pieces that might be used in surgery. Then when the saw blade 104 enters the bone 106 the current may be in the in the bone region 130. The current data may also be further processed to smooth out the data to reduce the influence of noise on the current measurement. An example of bone entry 118 can be seen in the saw motor current plot 114. In the segment shown by bone entry 118, the current goes up when the saw blade 104 enters the bone 106 and then drops when the saw blade 104 exits the bone 106. An example of event detector 120 is shown after a period of the saw blade 104 being in the bone 106. An event detector 120 may be used to determine these events. The event detector 120 receives the saw motor current plot 114 and pose information from the tracking system 112 via the data combiner 116.

Figure 2:
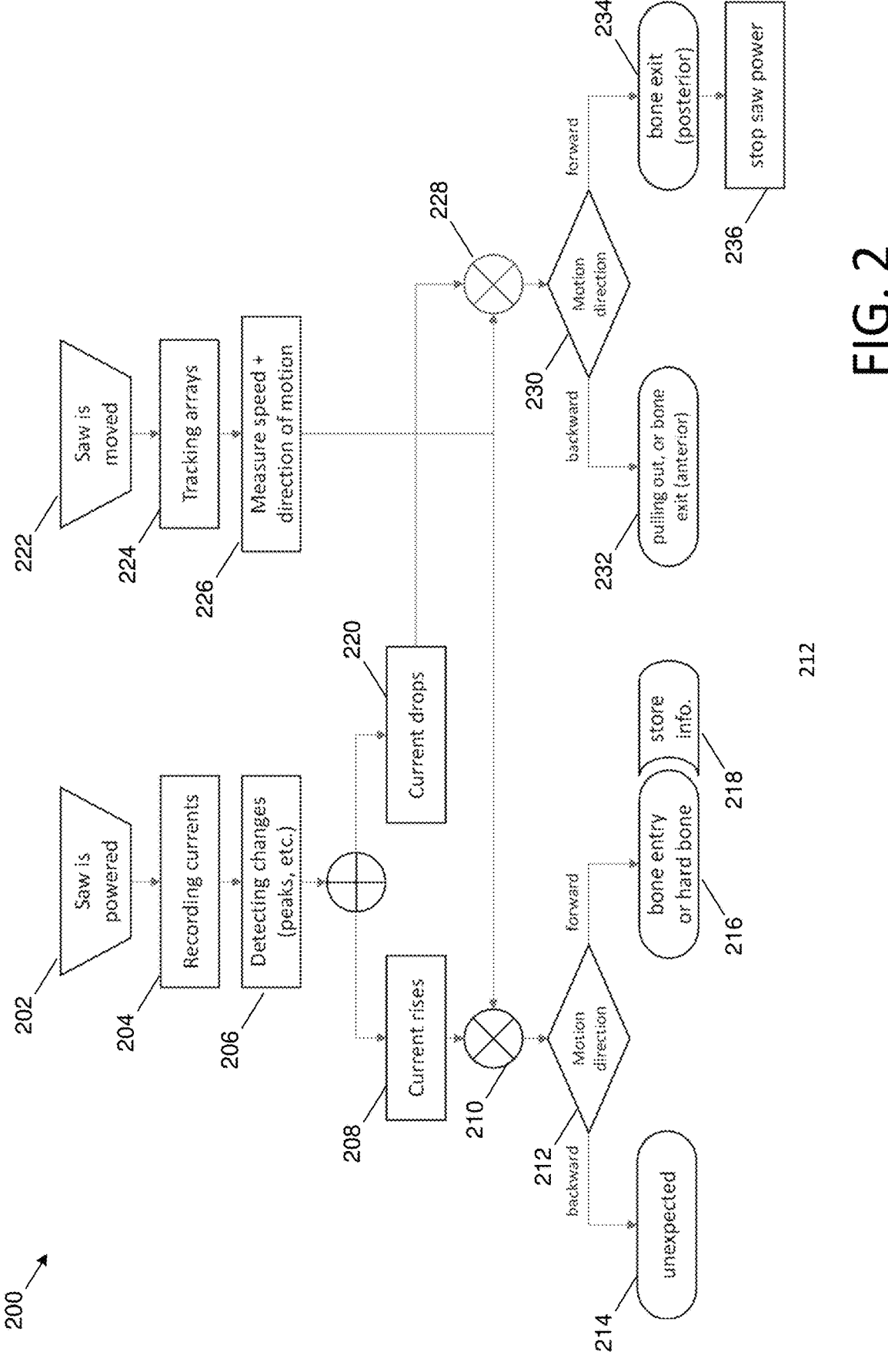
FIG. 2 illustrates a flow diagram of an embodiment of the operation of the event detector in the geofencing system.

FIG. 2 illustrates a flow diagram of an embodiment of the operation of the event detector in the geofencing system. During operation of the surgical saw 102 the cutting surface of the saw blade 104 will enter the bone 106 at a first surface and cut towards a second surface of the bone 106. If the saw blade 104 cuts far enough, it may cut through the second surface and possibly into adjacent soft tissue. At step 202 the surgical saw 102 is powered on. Then the event detector 120 starts recording or receiving current measurements from the surgical saw 102. The event detector 120 detects changes in the current such as step increases in the current, peaks, step decreases in the current, etc. at step 206. At step 208 the increase in the current is determined and characterized. The data combiner 210 combines the current increase informa-tion with a measure of the motion of the saw blade 104 relative to the bone. Then at step 212, the direction of the motion may be determined, i.e., is the saw blade 104 moving forward into the bone through the first surface and towards the second surface or backward out of the bone, i.e., the cutting edge is moving away from the second surface. If the current rises and the saw blade 104 is moving backward out of the bone 106, this is an unexpected situation and an alert may be provided to the user 214. Alternatively, the geofenc-ing system my cut power to the saw as a safeguard. If the current rises and the motion is indicated as forward into the bone, then step 216 indicates that the saw blade 104 is either entering the bone 106 or cutting the bone 106. At step 218 this information may be stored.

At step 222 the saw blade 104 is moved resulting in the tracking array 124 moving at step 224. The tracking system 112 can measure the speed and direction of the movement of the saw blade 104 at step 226. This measured speed and direction may be fed to the data combiner 210 and data combiner 228.

The data combiner 228 also receives the information indicating a current drop from step 220. The event detector 120 at step 230 will determine the direction of bone 106 like in step 212. If the current drops and the surgical saw 102 is moving backward, then an indication that the surgical saw

102 is pulling out or exiting the bone is provided 232. If the current drops and the surgical saw 102 is moving forward at step 234, this indicates that the saw blade 104 has reached soft tissue so the geofencing system cuts the power to the surgical saw 102 at step 236. This will prevent the saw blade 104 from inadvertently cutting into soft tissue near the bone. This is especially useful when the surgeon is unable to see the other side of a bone where soft tissue may reside next to the bone being cut.

Thresholds set for the different operating current regions of the surgical saw 102 may be based upon experimental data and analysis. The experimental data may also be analyzed to identify specific patterns and/or shapes of the current profile as the saw cuts the bone, for example, entering the bone, cutting the bone, being withdrawn from the bone, or exiting the bone into soft tissue. The detection of these patterns may be combined with the location of the surgical saw 102 and its direction and speed of motion to determine if the cutting surface of the saw blade 104 has exited the bone and possible is cutting nearby soft tissue.

In other embodiments, surgical saw 102 current data and motion data may be recorded and annotated for the events of entering the bone, cutting the bone, being withdrawn from the bone, or exiting the bone into soft tissue. This data then may be used to train a machine learning model that identifies specific situations where the bone 106 engages soft tissue, and this determination is used to stop the operation of the saw blade 104.

The geofencing system may learn the currents needed to cut the bone of a specific patient. For example, cuts that do not need geofencing may first be performed, where the geofencing system can learn/measure the current levels that correspond to the cortical and cancellous bone for this patient. Then the geofencing system can use this information to update the thresholds used later to detect the exit of the bone during the posterior cut where geofencing is needed.

The geofencing system may record/remember where the blade went through the bone and maintain a map or infor-mation regarding where the bone was. Because if the saw handpiece moves backward and then forward again, the geofencing system should remember that the saw is inside the bone despite the fact that the current will be very low.

Other analysis techniques may also be used to detect when the current indicates that the saw blade 104 has engaged or will be engaging soft tissue near the bone 106.

Figure 3:
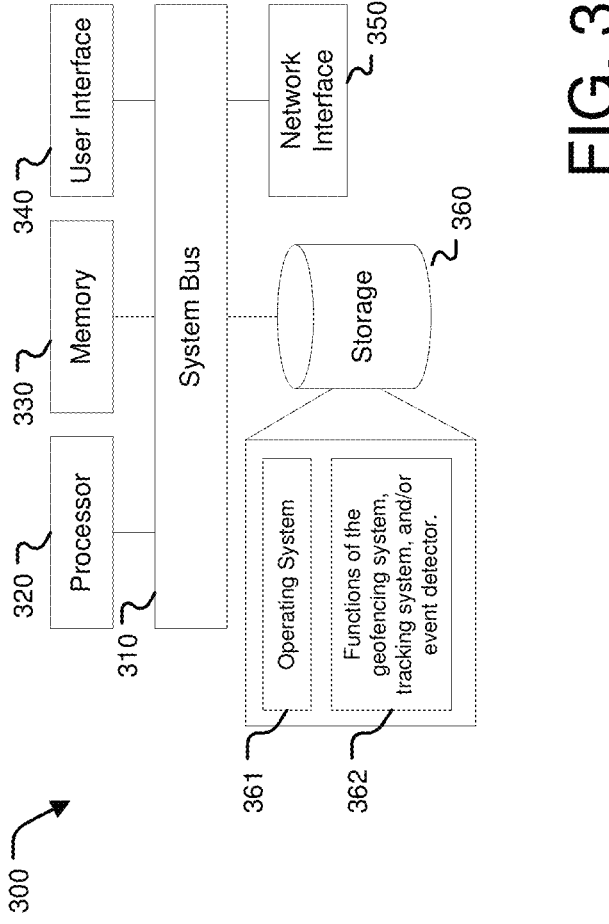
FIG. 3 illustrates an exemplary hardware diagram for implementing geofencing system, tracking system, or event detector.

FIG. 3 illustrates an exemplary hardware diagram 300 for implementing geofencing system, tracking system 112, or event detector 120. As shown, the device 300 includes a processor 320, memory 330, user interface 340, network interface 350, and storage 360 interconnected via one or more system buses 310. It will be understood that FIG. 3 constitutes, in some respects, an abstraction and that the actual organization of the components of the device 300 may be more complex than illustrated.

The processor 320 may be any hardware device capable of executing instructions stored in memory 330 or storage 360 or otherwise processing data. As such, the processor may include a microprocessor, microcontroller, graphics processing unit (GPU), neural network processor, field pro-grammable gate array (FPGA), application-specific inte-grated circuit (ASIC), or other similar devices.

The memory 330 may include various memories such as, for example L1, L2, or L3 cache or system memory. As such, the memory 330 may include static random-access memory (SRAM), dynamic RAM (DRAM), flash memory, read only memory (ROM), or other similar memory devices.

The user interface 340 may include one or more devices for enabling communication with a user such as an administrator. For example, the user interface 340 may include a display, a touch interface, a mouse, and/or a keyboard for receiving user commands. In some embodiments, the user interface 340 may include a command line interface or graphical user interface that may be presented to a remote terminal via the network interface 350.

The network interface 350 may include one or more devices for enabling communication with other hardware devices. For example, the network interface 350 may include a network interface card (NIC) configured to communicate according to the Ethernet protocol or other communications protocols, including wireless protocols. Additionally, the network interface 350 may implement a TCP/IP stack for communication according to the TCP/IP protocols. Various alternative or additional hardware or configurations for the network interface 350 will be apparent.

The storage 360 may include one or more machine-readable storage media such as read-only memory (ROM), random-access memory (RAM), magnetic disk storage media, optical storage media, flash-memory devices, or similar storage media. In various embodiments, the storage 360 may store instructions for execution by the processor 320 or data upon with the processor 320 may operate. For example, the storage 360 may store a base operating system 361 for controlling various basic operations of the hardware 300. The storages 362 may include instructions for carrying out the functions of the geofencing system, the tracking system, and/or the event detection.

It will be apparent that various information described as stored in the storage 360 may be additionally or alternatively stored in the memory 330. In this respect, the memory 330 may also be considered to constitute a "storage device" and the storage 360 may be considered a "memory." Various other arrangements will be apparent. Further, the memory 330 and storage 360 may both be considered to be "non-transitory machine-readable media." As used herein, the term "non-transitory" will be understood to exclude transitory signals but to include all forms of storage, including both volatile and non-volatile memories.

The system bus 310 allows communication between the processor 320, memory 330, user interface 340, storage 360, and network interface 350.

While the host device 300 is shown as including one of each described component, the various components may be duplicated in various embodiments. For example, the processor 320 may include multiple microprocessors that are configured to independently execute the methods described herein or are configured to perform steps or subroutines of the methods described herein such that the multiple processors cooperate to achieve the functionality described herein.

The foregoing disclosure provides illustration and description but is not intended to be exhaustive or to limit the aspects to the precise form disclosed. Modifications and variations may be made in light of the above disclosure or may be acquired from practice of the aspects. As used herein, the term "component" is intended to be broadly construed as hardware, firmware, and/or a combination of hardware and software. As used herein, a processor is implemented in hardware, firmware, and/or a combination of hardware and software.

As used herein, satisfying a threshold may, depending on the context, refer to a value being greater than the threshold, greater than or equal to the threshold, less than the threshold, less than or equal to the threshold, equal to the threshold, not equal to the threshold, and/or the like. It will be apparent that systems and/or methods described herein may be implemented in different forms of hardware, firmware, and/or a combination of hardware and software. The actual specialized control hardware or software code used to implement these systems and/or methods is not limiting of the aspects. Thus, the operation and behavior of the systems and/or methods were described herein without reference to specific software code—it being understood that software and hardware can be designed to implement the systems and/or methods based, at least in part, on the description herein.

As used herein, the term "non-transitory machine-readable storage medium" will be understood to exclude a transitory propagation signal but to include all forms of volatile and non-volatile memory. When software is implemented on a processor, the combination of software and processor becomes a specific dedicated machine.

Because the data processing implementing the embodiments described herein is, for the most part, composed of electronic components and circuits known to those skilled in the art, circuit details will not be explained in any greater extent than that considered necessary as illustrated above, for the understanding and appreciation of the underlying concepts of the aspects described herein and in order not to obfuscate or distract from the teachings of the aspects described herein.

Unless stated otherwise, terms such as "first" and "second" are used to arbitrarily distinguish between the elements such terms describe. Thus, these terms are not necessarily intended to indicate temporal or other prioritization of such elements.

It should be appreciated by those skilled in the art that any block diagrams herein represent conceptual views of illustrative hardware embodying the principles of the aspects.

While each of the embodiments are described above in terms of their structural arrangements, it should be appreciated that the aspects also cover the associated methods of using the embodiments described above.

Unless otherwise indicated, all numbers expressing parameter values and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

Even though particular combinations of features are recited in the claims and/or disclosed in the specification, these combinations are not intended to limit the disclosure of various aspects. In fact, many of these features may be combined in ways not specifically recited in the claims and/or disclosed in the specification. Although each dependent claim listed below may directly depend on only one claim, the disclosure of various aspects includes each dependent claim in combination with every other claim in the claim set. A phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

No element, act, or instruction used herein should be construed as critical or essential unless explicitly described as such. Also, as used herein, the articles "a" and "an" are intended to include one or more items and may be used interchangeably with "one or more." Furthermore, as used herein, the terms "set" and "group" are intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," and/or the like are intended to be open-ended terms. Further, the phrase "based on" is intended to mean "based, at least in part, on" unless explicitly stated otherwise.

The invention claimed is:

1. A geofencing system for a surgical handpiece with a cutting surface, comprising:

a motion tracking system configured to track a location of the surgical handpiece including a motor; and an event detector configured to:

receive a motor current measurement signal indicating a motor current usage of the motor of the surgical handpiece;

receive motion information regarding the surgical handpiece from the motion tracking system;

determine if the cutting surface has exited a second surface of a bone opposite a first surface where the cutting surface entered the bone based upon the motor current measurement signal and the motion information;

stop the surgical handpiece when it is determined that the cutting surface has exited the second surface of the bone;

determine whether the motor current usage has increased and the cutting surface is moving backward out of the bone; and generate an alert when it is determined that the motor current usage has increased and the cutting surface is moving backward out of the bone.

2. The geofencing system of claim 1, wherein the motion information includes a speed and direction of motion of the cutting surface.

3. The geofencing system of claim 2, wherein determining if the cutting surface has exited the second surface of the bone includes determining that the motor current usage of the motor of the surgical handpiece has dropped and that the direction of motion is towards the second surface.

4. The geofencing system of claim 3, wherein determining that the motor current usage of the motor of the surgical handpiece has dropped includes determining that a value of the motor current usage has dropped below a threshold value.

5. The geofencing system of claim 2, wherein determining if the cutting surface has exited the second surface of the bone includes identifying a pattern in the motor current usage of the motor the surgical handpiece indicative of the cutting surface exiting the second surface and that the direction of motion is towards the second surface.

6. The geofencing system of claim 2, wherein the event detector is further configured to determine that a value of the motor current usage has increased and that the direction of motion is towards the second surface to indicate that the surgical handpiece has entered the bone.

7. The geofencing system of claim 1, wherein determining if the cutting surface has exited the second surface of the bone is based on the motor current measurement signal wherein the motor current measurement signal is obtained when the surgical handpiece is operated outside the bone or when performing a cut on a patient that does not require geofencing.

8. A method of geofencing a surgical handpiece with a cutting surface, comprising:

receiving a motor current measurement signal indicating a current usage of a motor of the surgical handpiece;

receiving motion information regarding the surgical handpiece from a motion tracking system;

determining if the cutting surface has exited a second surface of a bone opposite a first surface where the cutting surface entered the bone based upon the motor current measurement signal and the motion information;

stopping the surgical handpiece when it is determined that the cutting surface has exited the second surface of the bone;

determining whether the motor current usage has increased and the cutting surface is moving backward out of the bone; and generating an alert when it is determined that the motor current usage has increased and the cutting surface is moving backward out of the bone.

9. The method of claim 8, wherein the motion information includes a speed and direction of motion of the cutting surface.

10. The method of claim 9, wherein determining if the cutting surface has exited the second surface of the bone includes determining that the current usage of the motor of the surgical handpiece has dropped and that the direction of motion is towards the second surface.

11. The method of claim 10, wherein determining that the current usage of the motor of the surgical handpiece has dropped includes determining that a value of the current usage has dropped below a threshold value.

12. The method of claim 9, wherein determining if the cutting surface has exited the second surface of the bone includes identifying a pattern in the motor current usage of the motor of the surgical handpiece indicative of the cutting surface exiting the second surface and that the direction of motion is towards the second surface.

13. The method of claim 9, further comprising determining that a value of the motor current usage has increased and that the direction of motion is towards the second surface to indicate that the surgical handpiece has entered the bone.

14. The method of claim 9, wherein determining if the cutting surface has exited the second surface of the bone is based on the motor current measurement signal wherein the motor current measurement signal is obtained when the surgical handpiece is operated outside the bone or when performing a cut on a patient that does not require geofencing.

15. A geofencing system for a surgical handpiece including a motor and a cutting surface, comprising:

a motion tracking system configured to track a location of the surgical handpiece; and an event detector configured to:

receive a motor current measurement signal indicating a motor current usage of the motor;

receive motion information regarding the surgical handpiece from the motion tracking system;

determine whether the motor current usage has increased and the cutting surface is moving backward out of a bone; and generating an alert responsive to determining that the motor current has increased and the cutting surface is moving backward out of the bone.

16. The geofencing system of claim 15, wherein the event detector is further configured to:

determine whether the cutting surface has exited a second surface of the bone opposite a first surface where the cutting surface entered the bone based, at least in part, on the motor current measurement signal and the motion information;

stop the surgical handpiece when it is determined that the cutting surface has exited the second surface of the bone; and process the motor current signal to reduce the influence of noise on the motor current signal.

\* \* \* \* \*